(12) United States Patent
Schmilovitch et al.

(10) Patent No.: US 7,236,237 B2
(45) Date of Patent: Jun. 26, 2007

(54) SPECTROSCOPIC FLUID ANALYZER

(75) Inventors: Zeev Schmilovitch, Yehud (IL); Gil Katz, Kibbutz Afikim (IL); Ephraim Maltz, Kirvat Ono (IL); Martin I. Kutscher, Mishmar Ha'Yarden (IL); Moran Sarig, Kibbutz Afikim (IL); Ilan Halachmi, Kfar Yehoshua (IL); Aharon Hoffman, Ramat Gan (IL); Haim Egozi, Hod Hasharon (IL); Eithan Uner, Kibbutz Afikim (IL)

(73) Assignees: S.A.E. Afikim Computerized Dairy Management System, Kibbutz Afikim (IL); Agricultural Research Organization of the State of Israel Ministry of Agriculture, Kibbutz Afikim (IL)

( * ) Notice: Subject to any disclaimer, the term of this patent is extended or adjusted under 35 U.S.C. 154(b) by 409 days.

(21) Appl. No.: 10/811,534

(22) Filed: Mar. 29, 2004

(65) Prior Publication Data
US 2004/0179194 A1    Sep. 16, 2004

Related U.S. Application Data

(63) Continuation-in-part of application No. 09/996,625, filed on Nov. 28, 2001, now abandoned, and a continuation-in-part of application No. PCT/IL02/00892, filed on Nov. 7, 2002.

(30) Foreign Application Priority Data
Nov. 8, 2001    (IL) .................................... 146404

(51) Int. Cl.
*G01N 21/00* (2006.01)
*G01N 1/10* (2006.01)
*B32B 5/02* (2006.01)
*B32B 27/04* (2006.01)
*B32B 27/12* (2006.01)
*A01J 3/00* (2006.01)
*A01J 5/00* (2006.01)

(52) U.S. Cl. ......................... 356/73; 356/246; 356/337; 356/440; 422/82.05; 422/82.09; 119/14.14

(58) Field of Classification Search .................... None
See application file for complete search history.

(56) References Cited

U.S. PATENT DOCUMENTS 3,869,214 A * 3/1975 Egli et al. ................... 356/246

(Continued)

FOREIGN PATENT DOCUMENTS

EP              595409            5/1994

(Continued)

OTHER PUBLICATIONS http://www.foodsci.uoguelph.ca/dairyedu/chem.html, Oct. 24, 2001.

(Continued)

*Primary Examiner*—Samuel A. Turner
*Assistant Examiner*—Gordon J. Stock, Jr.
(74) *Attorney, Agent, or Firm*—Nixon & Vanderhye P.C.

(57) ABSTRACT

An NIR spectroscopy fluid analyzing system using a series of LED's, each having its own preselected center wavelength, as illumination sources. These wavelengths have overlapping spectral widths, such that the measurement covers a broad spectrum. The LED's illuminate the fluid sample sequentially, and subsequently the transmission absorbance through the sample and the reflectance or scattering from the sample is measured for the wavelength range of each LED. The measurements are performed using photodetectors. The concentrations of component parts of the fluid are expressed in the form of a polynomial, which is a function of the measured transmitted and/or reflected intensities, and of empirical coefficients, which are extracted by prior statistical analysis on measured intensities obtained from a large number of test samples having known concentrations of the component. A novel sample chamber, capable of performing optical absorption measurements on a flowing sample of fluid, is described.

26 Claims, 3 Drawing Sheets

U.S. PATENT DOCUMENTS

| | | | | |
|---|---|---|---|---|
| 3,946,239 | A | * | 3/1976 | Salzman et al. .......... 250/461.2 |
| 4,200,802 | A | * | 4/1980 | Salzman et al. .......... 250/461.2 |
| 4,818,493 | A | * | 4/1989 | Coville et al. ............... 422/102 |
| 5,116,119 | A | | 5/1992 | Brayer ......................... 356/28 |
| 5,581,086 | A | | 12/1996 | Ben-menachem ........... 250/343 |
| 5,743,209 | A | | 4/1998 | Bazin et al. .............. 119/14.08 |
| 5,816,190 | A | | 10/1998 | Van derLely ............. 119/14.08 |
| 6,407,813 | B1 | * | 6/2002 | Lovette et al. ............... 356/338 |
| 7,092,084 | B2 | * | 8/2006 | Payne ......................... 356/246 |

FOREIGN PATENT DOCUMENTS

| | | |
|---|---|---|
| EP | 728413 | 8/1996 |
| RU | 2077198 | 4/1997 |
| WO | WO 96/31764 A1 * | 10/1996 |
| WO | WO 98/02720 | 1/1998 |
| WO | WO 98/43070 | 10/1998 |
| WO | WO 00/64242 A1 * | 11/2000 |

OTHER PUBLICATIONS

Manabu Kitazawa, et al., "Ultraviolet generation at 266 nm in a novel organic nonlinear optical crystal: L-pyrrolidone-2-carboxylic acid", Appl. Phys. Lett. 64(9), May 9, 1994.

Jun Kawamata, et al., "Salient nonlinear optical properties of novel organic crystals comprising πconjugated ketones", Appl. Phys. Lett. 66(23), Jun. 5, 1995.

Kazuhisa Yamamoto, et al., "High power blue light generation by frequency doubling of a laser diode in a periodically domain-inverted LiTaO3 waveguide", Appl. Phys. Lett. 62(21), May 24, 1993.

Kiminori Mizuuchi, et al., "Second-harmonic generation of blue light in a LiTaO3 waveguide", Appl. Phys. Lett. 58(24), Jun. 17, 1991.

R.W. Verhoef, et al., "Repulsive interactions of potassium on Re(001)", J. Chem. Phys. 106(22), Jun. 8, 1997.

E.D. Mishina, et al., "Local probing of the polarization state in thin Pb(ZrTi)O3 films during polarization reversal", Appl. Phys. Lett. 78(6), Feb. 5, 2001.

Beth L. Smiley, et al., "Near UV optical second harmonic generation studies of surface-adsorbed tryptophan residues", J. Chem. Phys. 103(8), Aug. 22, 1995.

R. Tsenkova, et al., "Near Infra-Red Spectroscopy for Dairy Management: Measurement of Unhomogenized Milk Composition", Published in Journal of Dairy Science, vol. 82, pp. 2344-2351. 1999.

Z. Schmilovitch, et al., "Fresh raw Milk Analysis by NIR Spectroscopy", Published in Proceedings of the International Symposium on the Prospects for Automatic Milking, Wageningen, Netherlands, EAAP Publication No. 65, pp. 193-198, 1992.

Z. Schmilovitch, et al., "Low Cost Near Infra-red Sensor for On-Line Milk Composition Measurement", Published in the Proceedings of the XIV Memorial CIGR World Congress, 2000, Tsukuba, Japan.

* cited by examiner

FIG. 4
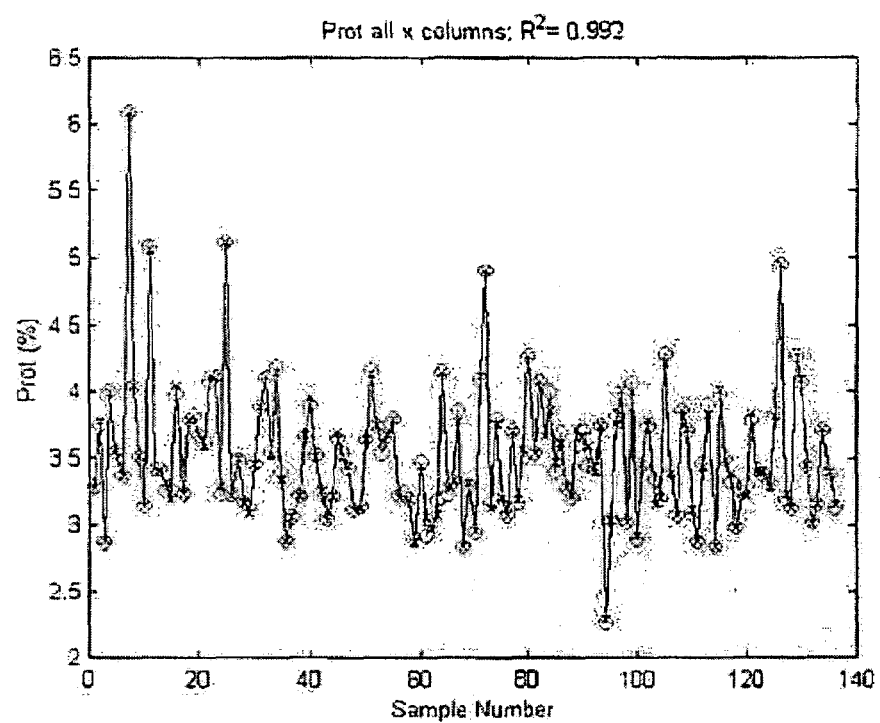
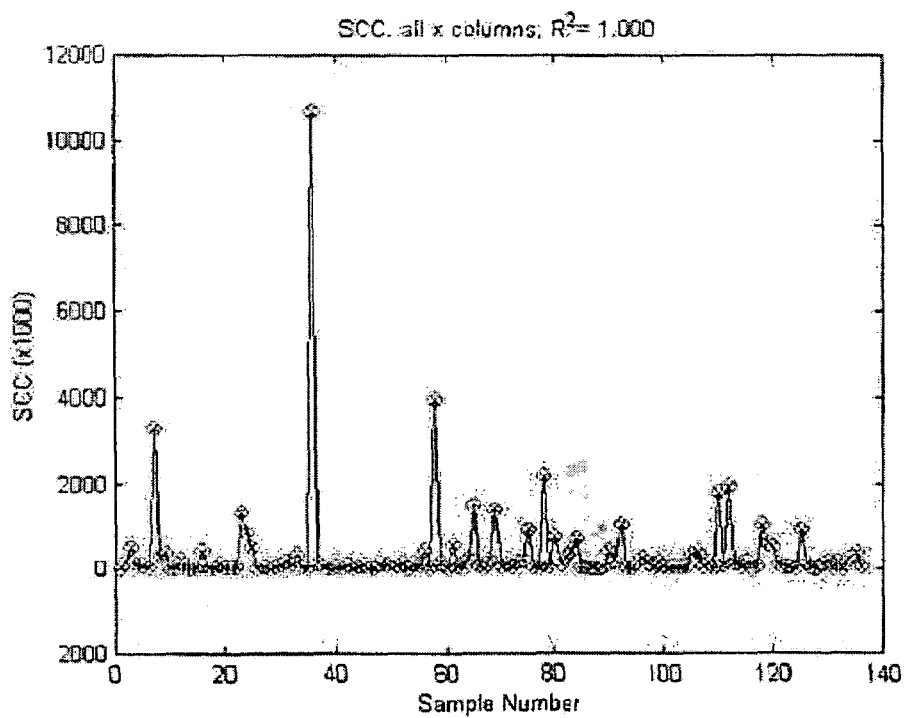
FIG. 5

SPECTROSCOPIC FLUID ANALYZER

This application is a continuation-in-part of application Ser. No. 09/996,625 filed on Nov. 28, 2001 now abandoned, and a continuation-in-part of PCT/IL02/00892 filed on Nov. 7, 2002, which designated the U.S., claims the benefit thereof and incorporates the same by reference.

FIELD OF THE INVENTION

The present invention relates to the field of the quantitative analysis of milk, using spectroscopic techniques in the visible and near infra-red band, especially for on-line assessment of component parts of milk during the milking process.

BACKGROUND OF THE INVENTION

Measurement of the component parts of milk, and real time knowledge of the results of these measurements, is an important factor in the efficient management of a dairy farm. Knowledge of the levels of almost all of the various component parts of the milk is important for different aspects of the herd management. These components include fat, total protein, casein, lactose, somatic cells, blood, progesterone, amino-acids urea, and nucleic acid. The fat and protein content, for instance, are major factors in determining the price that the farmer will obtain for his milk, because they are important economic indicators of the overall milk quality. Changes in these values can indicate to the farmer an incorrect diet. Thus, changes in the fat content could indicate an imbalance in the forage-to-concentrate ratio in the feed; low total protein level may indicate a dietetic energy deficiency; the somatic cell count and the blood count may be used as diagnostic indicators of a specific clinical state of the cow; and fluctuations in lactose content, which is generally very stable for a cow, can indicate the presence of mastitis.

Several methods are described in the prior art for performing on-line milk analysis, with the object of more efficient milk production and herd management. The use of near infra-red (NIR) spectroscopy for analyzing milk has been known for almost 15 years, and the early methods used laboratory-type NIR spectrometers for analyzing the milk off-line. A number of such instruments are available commercially, but they are expensive, and their use is thus generally limited to centralized laboratories, to which the farmer would send milk samples for testing typically only once a month.

In the article "Near Infra-Red Spectroscopy for Dairy Management: Measurement of Unhomogenized Milk Composition" by R. Tsenkova et al., published in Journal of Dairy Science, Vol. 82, pp. 2344–2351, 1999, there is proposed a method whereby the milk content is spectroscopically analyzed in the NIR range of from 400 nm to 2500 nm. A proposal is made therein to use fiberoptic probes and relatively inexpensive silicon detectors for detecting the radiation within the range 700 nm to 1100 nm, thereby making the method affordable enough to be applied at the milking station for real-time analysis during milking. However, no details are given of an apparatus suitable for performing this analysis using such silicon detectors. Furthermore, although the use of inexpensive detectors is proposed, no mention is made of the sources that could be used with these detectors to provide the NIR illumination.

The article presents an analysis and comparison of the results obtained in the 1100 to 2400 nm spectral range, to those obtained in the 700 to 1100 nm spectral range, where inexpensive silicon detectors can be used. Essentially continuous measurements (every 2 nm) were made across the whole of these spectral ranges. Though not specifically stated in the article, such spectral coverage can generally be obtained from the internal blackbody illuminating source of most NIR spectrometers. The methods described in the Tsenkova et al. article are largely directed at statistical methods of extracting the desired concentration levels from the overall absorption spectra. A commercial software program was used to develop models for determining fat, total protein and lactose content, and calibration of the models was performed using the Partial Least Squares (PLS) regression technique.

Further descriptions of methods of milk analysis using NIR spectroscopy are given in the articles "Fresh raw milk composition analysis by NIR spectroscopy" by Z. Schmilovitch et al, published in Proceedings of the International Symposium on the Prospects for Automatic Milking, Wageningen, Netherlands, EAAP Publication No. 65, pp. 193–198 (1992), and in "Low Cost Near Infra-red Sensor for On-line Milk Composition Measurement" by Z. Schmilovitch et al., published in the Proceedings of the XIV Memorial CIGR World Congress, 2000, Tsukuba, Japan, some of the authors of which are co-applicants for the present invention.

The spectroscopic measurements themselves in the above-mentioned Tsenkova et al article were performed off-line on collected samples, using a commercial NIR spectroscopic milk analyzer, the Milko-Scan, supplied by Foss-Electric A/S, Hillerod, Denmark. The cost of such instruments is such that they are only generally feasibly economical for installation in central laboratories, and not in every cowshed, let alone at every milking station.

There therefore exists an important need for an inexpensive and simple apparatus and method for the on-line qualitative analysis of milk, which will be sufficiently inexpensive that it can be widely used to enable real-time data to be obtained during the milking process, even at each milking station, but without significantly compromising the accuracy of the measurements required for efficient dairy herd management. Furthermore, the apparatus must be capable of performing its analyses on the type of milk flows typically obtained from milking machines. Such flows are highly pulsed in nature, and generally very turbulent, such that a conventional optical sensing path which measures the optical transmission through the flow from side to side of the flow channel is of limited use.

The disclosures of all publications mentioned in this section and in the other sections of the specification, and the disclosures of all documents cited in the above publications, are hereby incorporated by reference, each in its entirety.

SUMMARY OF THE INVENTION

The present invention seeks to provide a novel fluid analyzing system, which uses a near infra-red spectroscopy technique for determining the percentage concentrations of the constituent parts of the fluid. The analyzing system is particularly useful for the analysis of milk. The NIR measurement technique, according to various preferred embodiments of the present invention, differs in a number of ways from techniques previously used for quantitative analysis of milk.

According to a first preferred embodiment of the present invention, the source of incident optical beam for the spectroscopic absorption measurements is made up of a series of light emitting diodes (LED's), each having its own preselected center wavelength. These wavelengths are preferably selected such that the LED's have overlapping spectral widths, such that the entire spectrum over which measurements are to be taken is covered. Since the typical spectral width of a LED in these spectral regions is of the order of up to 40 to 60 nm half-width, according to one preferred embodiment of the present invention, a series of 10 LED's covers the desired spectral measurement range of the visible and NIR spectral ranges from 450–950 nm. The LED's illuminate the fluid sample sequentially, and the transmission absorbance through the sample is measured by means of photodetectors. According to another preferred embodiment of the present invention, in addition to the transmission absorption measurements, the reflectance or scattering from the sample is measured for the wavelength range of each LED.

LED's, like the photodiodes described in the Tsenkova et al. article, are inexpensive light sources, readily available and conveniently applicable. The use of a series of LED's as light sources, according to this preferred embodiment of the present invention, thus complements the previously proposed use of inexpensive photodetectors in enabling the construction of an inexpensive and convenient-to-use NIR absorption spectrometer for on-line milk analysis.

There is also provided, according to yet another preferred embodiment of the present invention, a method of exposing the sample cavity to perform NIR spectroscopy on a fluid mixture such as milk, using a plurality of LED's which cover the visible and NIR spectral ranges. The LED's illuminate the fluid sample sequentially, and the transmission absorbance is measured for each incident LED. Additionally and preferably, the scattered or reflected radiation is detected at an angle to the incident radiation. According to one preferred embodiment, it is measured at right angles to the incident radiation. According to a second preferred embodiment, back-reflected or scattered radiation is detected by positioning the detector essentially at the same location as the input beam. This enables a convenient arrangement of source and detector to be used.

In conventional absorption spectroscopy, the absorptions are related to the concentrations of the component parts of the fluid by means of the familiar Beer-Lambert law, which assumes an exponential relationship between the light intensity absorption and concentration. According to the preferred methods of the present invention, these concentrations of the component parts of the fluid are expressed in the form of expressions, which are preferably a polynomial expression, the expressions being functions of the measured transmitted and/or reflected or absorbed intensities, and of empirical coefficients, which are extracted preferably by performing a Partial Least Squares (PLS) or a Ridge Least Squares (RLS) regression technique on measured intensities, obtained by measuring a large number of test samples having known concentrations of the component, as is well known in the art. However, according to further preferred embodiments of the present invention, the regression method used differs in two respects from the previously used techniques, in that:

(i) it is performed on a polynomial of up to third order in intensities, where the second order intensity terms arise from the second harmonic measurements and the third order intensity terms arise from the third order harmonic measurements; and (ii) the polynomial includes terms arising both from transmission absorbance spectroscopy measurements and from reflection spectroscopy.

Though in this preferred embodiment of the present invention, PLS or RLS regression techniques are proposed in order to extract the coefficients of the third order polynomial, it is to be understood that this technique is only one of several statistical techniques available for fitting such a polynomial to the absorbance data, and it is not intended that this invention be limited to the use of the PLS or the RLS technique for the statistical analysis. Furthermore, although a polynomial of third order in intensity is used in the embodiment described, it is to be understood that any higher order polynomial can be used, and that it is not intended that this invention be limited to the use of a third order polynomial in intensity.

The empirical coefficients thus obtained for each sample are stored as a database in the computing system memory, along with the component concentrations of the associated sample. When an unknown sample of milk is to be measured, during use of the system, the extraction of the concentrations of the constituents of the sample is preferably performed by a further statistical analysis method using the contents of this database, such as is known from chemometric analysis methods used in the analysis of multiple component chemical reaction dynamics.

The spectroscopic measurements are performed on the milk using a novel sampling chamber, constructed and operative according to a further preferred embodiment of the present invention. This sampling chamber has a recessed cavity, preferably adjoining the main flow conduit of the milk, and located in a generally downwards direction, such that it fills with a constantly changing sample of the flowing milk. This enables optical transmission measurements to be performed on a pulsating milk flow, without the pulsation and turbulence significantly affecting the accuracy of the measurement. The optical beam measurement path traverses the central area of this recessed cavity, with the source on one side and the transmission measurement detector on the other side. For the purpose of the scattering measurements, another detector is disposed, preferably at right angles to the optical beam path, to detect the beam scattered at 90 degrees by the milk in the sampling cavity. For the purpose of the back-scattering measurements, another detector is disposed, preferably at approximately the same location as the source LED's.

In accordance with yet another preferred embodiment of the present invention, there is provided a system for determining the concentration of at least one component of a fluid., The fluid comprises two or more components having different optical absorption properties, and the system comprises a sample cavity containing the fluid, a plurality of optical beam sources, one or more of which, when excited, emits an optical beam having an essentially continuum of wavelengths, two or more of the sources having different spectral ranges of emission, the sources being disposed such that the beam from the sources is incident on the fluid in the sample chamber., The system also comprises a first detector disposed such that it measures the intensity of the beam transmitted through the fluid, a second detector disposed such that it measures the intensity of the beam scattered from the fluid, a control system which excites at least two of the beam sources serially, such that the fluid is separately scanned with wavelengths of the optical beam of the two or more sources, and a computing system operative to determine the concentration of the one or more component of the fluid from the intensity of the beam transmitted through the fluid or the beam scattered by the fluid. The sources may preferably be light emitting diodes. The second detector may preferably be disposed such that it measures the intensity of the beam back-scattered or reflected from the fluid.

According to another preferred embodiment, in the above-mentioned system the computing system is operative to determine the concentration by fitting the intensity of the optical beam transmitted through the fluid and of the beam scattered from the fluid to a polynomial expression for the concentration of one of the components in terms of the intensities. The polynomial expression is preferably of at least second order in the transmitted and scattered intensities. Furthermore, the transmitted and scattered intensities may preferably be related to the concentration of the component by means of empirical coefficients determined by a statistical analysis of transmitted and scattered intensities obtained from a plurality of samples of the fluid having known concentrations of the component. This statistical analysis may preferably be a Partial Least Squares regression method or a Ridge Least Squares regression method. In addition, the empirical coefficients are preferably stored in a database, and the concentration is extracted from the transmitted and scattered intensities by means of statistical analysis methods operating on the database.

Any of the above-mentioned systems may preferably be utilized for analyzing milk, and the system may preferably determine the constitution of the milk on-line during the milking process.

According to even another preferred embodiment of the present invention, there is also provided a method of determining the concentrations of at least one component of a fluid, the fluid comprising at least two components having different optical absorption properties, comprising the steps of:

(a) exposing the fluid to an incident optical beam from a source essentially having a continuum of wavelengths of emission;
(b) measuring transmitted and scattered intensities of the incident beam by the fluid; and
(c) relating the intensities to a polynomial expression for the concentration of the component in terms of the intensities, the polynomial expression being at least second order in the transmitted and scattered intensities.

According to yet another preferred embodiment of the present invention, in the above-mentioned method, steps (a) and (b) may be repeated using a plurality of sources, each source having its own continuum of wavelengths. The polynomial expression may preferably be of third order in the transmitted and scattered intensities. Furthermore, the scattered intensities may be reflected intensities. In addition, the transmitted and scattered intensities may preferably be related to the concentration of the component by means of empirical coefficients, which are determined by a statistical analysis of transmitted and scattered intensities obtained from a plurality of samples of the fluid having known concentrations of the component. This statistical analysis may preferably be either a Partial Least Squares regression method, or a Ridge Least Squares regression method.

In the methods described above, the empirical coefficients may preferably be stored in a database, and the concentration extracted from the transmitted and scattered intensities by means of statistical analysis methods operating on the database.

In the above-described method, the exposed fluid is preferably milk.

There is also provided, according to yet another preferred embodiment of the present invention, a sampling chamber for performing optical measurements on a sample of a flowing fluid comprising a flow conduit for the passage of the fluid, a recessed cavity in fluid contact with the conduit and directed in a generally downward direction such that a sample of fluid in the conduit can enter the cavity, and an optical transmission path passing through the cavity in such a position that it lies outside the confines of the flow conduit.

In the above-described sampling chamber, the optical transmission path preferably comprises an entry port for inputting an optical beam from a source, and an exit port for directing the beam to a detector. The entry port and the exit port are preferably disposed such that the beam traverses a sample cavity linearly, thereby to perform transmission optical measurements on the sample. Alternatively and preferably, another exit port may be disposed at an angle to the direction of the optical beam, to cause optical scattering measurements on the sample. Furthermore, the exit port may be disposed essentially co-positional with the entry port to perform back-scattering optical measurements on the sample.

According to yet further embodiments of the present invention, the recessed cavity is such that the sample is repeatedly changed by the effects of the flow of the fluid in the conduit. The cavity is so formed and disposed so that the optical measurements are generally unaffected by turbulence or pulsation in the flow conduit.

In the above-mentioned sampling cavity, the optical measurements are preferably utilized to determine relative concentrations of components of the fluid.

Furthermore, the conduit is preferably a milk conduit. Additionally, according to another embodiment of the present invention, the optical transmission path includes fiberoptic cables or plastic optical guides.

BRIEF DESCRIPTION OF THE DRAWINGS

The present invention will be understood and appreciated more fully from the following detailed description, taken in conjunction with the drawings in which:

FIG. 3A is a side view of the sampling chamber, while FIG. 3B is a cross-section;

FIG. 4 is a graph showing the results of approximately 140 analyses of samples of milk, taken from different cows during milking for the protein concentration using a milk analyzer constructed and operative according to preferred methods of the present invention; and FIG. 5 is a graph showing the results of the analysis of approximately 140 samples of milk for the somatic cell count (SCC), using a milk analyzer constructed and operative according to a preferred embodiment of the present invention.

DETAILED DESCRIPTION OF PREFERRED EMBODIMENTS

Figure 1:
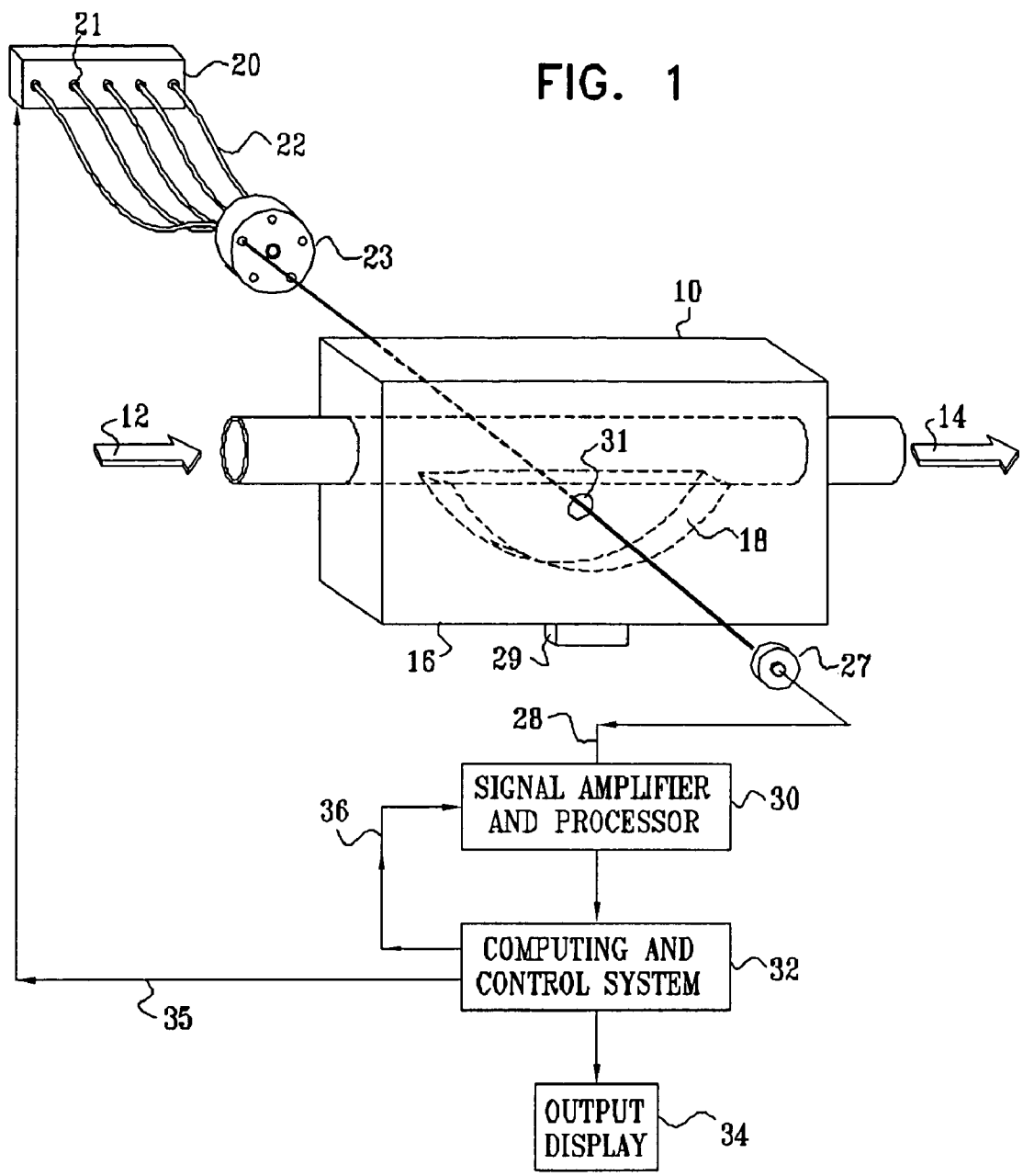
FIG. 1 is a schematic diagram of the optical measurement system of a spectroscopic milk analyzer, constructed and operative according to a preferred embodiment of the present invention.

Reference is now made to FIG. 1, which is a schematic illustration of a spectroscopic milk analyzer generally referenced 1 and its optical measurement system, according to one preferred embodiment of the present invention. The milk flows through a flow conduit or tube 10, typically from a milking station 12 towards a collection point 14. It is to be understood that the milk analyzer of the present invention could be advantageously incorporated at any other point in the milk flow path. A sampling chamber 16 is located in milk flow conduit 10, and a sample of the flowing milk collects in the sample cavity 18. The structure and operation of cavity 18 are described in more detail hereinbelow, in connection with FIGS. 3A and 3B.

Adjacent to cavity 18 is provided a light emitting diode (LED) array 20 which preferably incorporates a number of discrete LED emitters 21, each emitting at a different wavelength within the range to be used for the measurement. According to one preferred embodiment, the wavelengths of the LED's 21 used range from 450 nm to 950 nm, to cover the visible to NIR regions of the spectrum. According to this preferred embodiment, the light output from each LED 21 is transmitted by means of an optical fiber 22 to a rosette 23, where all fibers 22 are bundled together to form a compact source, which emits the wavelength of whichever LED, or LED's 21 are illuminated. In the center of rosette 23 there is located a back-scattering detector 24.

Figure 2:
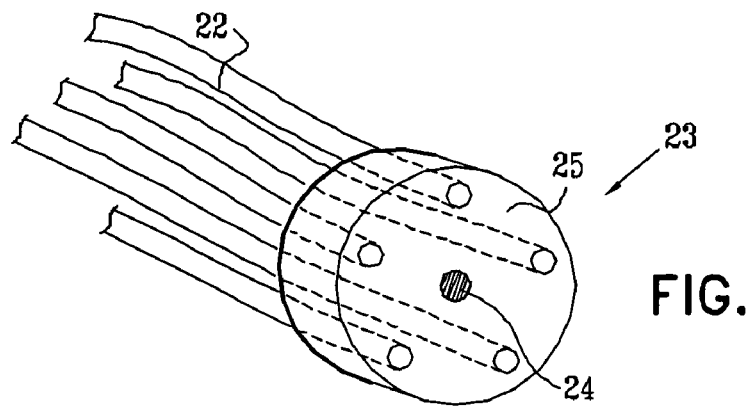
FIG. 2 is an enlarged view of the illumination rosette in the measurement system shown in FIG. 1.

Referring now to FIG. 2, which is a schematic view of the illumination rosette 23 of FIG. 1, enlarged to show the details more clearly. Ends 25 of fibers 22 which emit the LED illumination, are grouped as closely as possible to each other, so that the different wavelength sources are as close as possible to a single source. At the center of this bundle is positioned detector 24, for use in detecting back-scattered light. In operation, each of the LED's 21 is turned on sequentially, such that the spectrum of discrete wavelength points is measured sequentially. According to another preferred embodiment of the present invention, another detector 29 (as seen in FIG. 1) is positioned at an angle to the direction of the incident optical beam, so that scattering in directions other than that of back-scattered reflection can preferably be detected.

Referring now to FIG. 1, the light transmitted from source rosette 23 enters through an entry port (not shown) and passes through sample cavity 18 to be emitted through an exit port 31 to be detected, preferably by means of a silicon photo-detector 27 disposed adjacent to exit port 31. A detected signal 28 corresponding to the beam intensity is input into a signal amplification and processing system 30. This can optionally be operated as a phase sensitive detection system in order to provide optimum detection sensitivity, with the LED's modulated accordingly. The output intensities from the detection system are preferably fed to a computing and control system 32, where the spectra obtained are analyzed by methods according to other preferred embodiments of the present invention. Computing and control system 32 passes control information 35 to LED sources 21, to provide the modulation frequency, if used, and which is also input by means of control line 36 to the phase sensitive detector in the signal amplifying and processing system 30. Computing and control system 32 also controls the switching order and timing of the LED sources 21, for scanning the complete spectral range to be measured. Computing and control system 32 transfers the results of the analysis to output display 34 for display.

According to one preferred scanning program, each LED 21 is turned on for several milliseconds, and the absorption and/or scattering measurements are performed at that wavelength. In order to perform the measurements more rapidly, the transmission absorbance signal on detector 27 and the back-scattering signal on detector 24 are measured simultaneously. If a right-angled detector 29 is used, its signal is also measured simultaneously with the signals on detectors 24 and 27. A complete scan of all 10 of the LED's 21 takes approximately 250 msec with the research apparatus used to develop and measure the performance of the invention. Use of a high speed microprocessor running dedicated software for processing the signals, as would preferably be incorporated into a commercial milk analyzer 1, constructed according to the present invention, is expected to reduce the scan time.

The pulse rate of the milk flow through chamber 16 during milking is at most generally no faster than one milk pulse every two seconds. Since this repetition rate is generally significantly slower than the measurement scan rate, the absorbance/scattering measurements can preferably be repeated several times on each milk sample collected in sample cavity 18, and then averaged for each sample, thereby reducing the noise level of the measurements and increasing the accuracy with which the concentrations can be calculated.

According to a further preferred embodiment of the light generation and detection system of the present invention, the fiberoptic cables may be replaced with plastic light guides to form a less costly, more compact, and waterproof assembly. The light guides preferably have a siphon-like structure, having a 5 mm diameter at the LED end, tapering to 1 mm at the sample chamber.

In order to overcome physical size constraints, the 10 LED's 21 are preferably divided into two groups of five, each rosette 23 having only 5 LED's 21 and its own central detector 24, and each rosette 23 being disposed on opposite sides of sample cavity 18. According to this preferred embodiment, illumination and detection is performed sequentially from both sides of sampling cavity 18, with the 5 LED's 21 in each rosette 23. Detector 24 of each rosette collects back scattered light from its own LED's 21 and transmitted light from the LED's 21 of the opposite rosette 23. According to this preferred embodiment, the function of detector 29, if used, remains unchanged.

A major problem in analyzing the spectrum of a multi-component fluid such as milk arises from the overlap of the individual absorption and scattering spectra of each of the separate components. Furthermore, according to the illumination method of the present invention where the spectral width of the LED sources 21 may be such as to include a number of such individual absorption and scattering spectral lines, in order to quantitatively analyze the milk for its separate constituents a method must be provided for extracting this information about the identification of the lines present, and determination of their intensity. The method must be capable of doing this to a plurality of lines "hidden" within the intensity measurements obtained from the relatively broad bandwidth LED sources 21.

According to a preferred method of the present invention, a high order polynomial expression is used to express the concentrations, C, of the various milk constituents in sample cavity 18 in terms of the measured transmitted and reflected (scattered) light intensities for each LED measurement, each intensity term appearing with an empirical coefficient. According to one preferred embodiment, the polynomial may be of the form:

$$C\% = \Sigma a_{tj} I_{tj} + \Sigma b x_{tj} I^2_{tj} + \Sigma c x_{tj} I^3_{tj} + \ldots + \Sigma a x_{rj} I_{rj} + \Sigma b x_{rj} I^2_{rj} + \Sigma c x_{rj} I^3_{rj} +$$

where:

j=1–10, representing 10 discrete light sources in the NIR and visible spectrum;

$I_{tj}$=intensity of the light from source j, detected on the transmittance photo-detector;

$I_{rj}$=intensity of the light from source j, detected on the reflectance photo-detector;

C %=concentration of constituent C; and $ax_{tj}, bx_{tj}, cx_{tj} \ldots, ax_{rj}, bx_{rj}, cx_{rj} \ldots,$ =empirical coefficients, relating the intensities of the light detected to the concentration of the constituent C. According to one particularly preferred embodiment, a third order polynomial is used, and only coefficients up to $cx_{tj}$ and $cx_{rj}$ are used.

The values of these empirical coefficients are initially experimentally determined preferably by using a statistical analysis method, such as by performing PLS regression or RLS calculations on a large database of absorption and reflectance data acquired experimentally from a large number of samples of milk with different and variable constituents. To provide a sufficiently broad database, the samples are preferably obtained from several hundred different cows. The data are obtained from absorption and reflectance measurements made using the light emitted from the ten LED's. The constituents of each sample of milk are independently determined, preferably using a standard spectrophotometric method, and these known constituent concentrations are then used to extract the empirical coefficients by using a preferred statistical analysis method.

Once these coefficients are known they are stored, along with the concentrations of the sample with which they are associated, as a reference database in the computing system memory for use in measurements of unknown samples. The extraction of the concentrations of the constituents from an unknown sample of milk is preferably performed by a further statistical analysis method, comparing the measured intensities with the contents of the database, such as is known from chemometric analysis methods used in the analysis of multiple component chemical reaction dynamics. According to one preferred embodiment of the present invention, the analyzer uses ten LED sources 21, such that 20 measurement signals are obtained from each unknown sample of milk, 10 from transmission measurements, one from each of the 10 LED's 21, and 10 from reflectance or back-scattering measurements, one from each of the 10 LED's 21. These 20 measurement signals, each at their known wavelength range, are then related, preferably by means of the statistical analysis chemometric-type methods, to a large database of stored spectral curves related to various milk compositions, and from the analysis a unique set of concentrations of the constituents of the milk sample is determined. This method of calibration and analysis thus allows the use of inexpensive LED's 21 with their non-uniform wide spectral range as light sources, rather than a more discrete and monochromatic source of light, such as a laser, as is used in some prior art optical fluid analyzers.

Results of these concentration analyses for all of the milk components detected, are preferably printed or displayed on output display 34 and transferred to a herd management system for analysis.

Figure 3A:
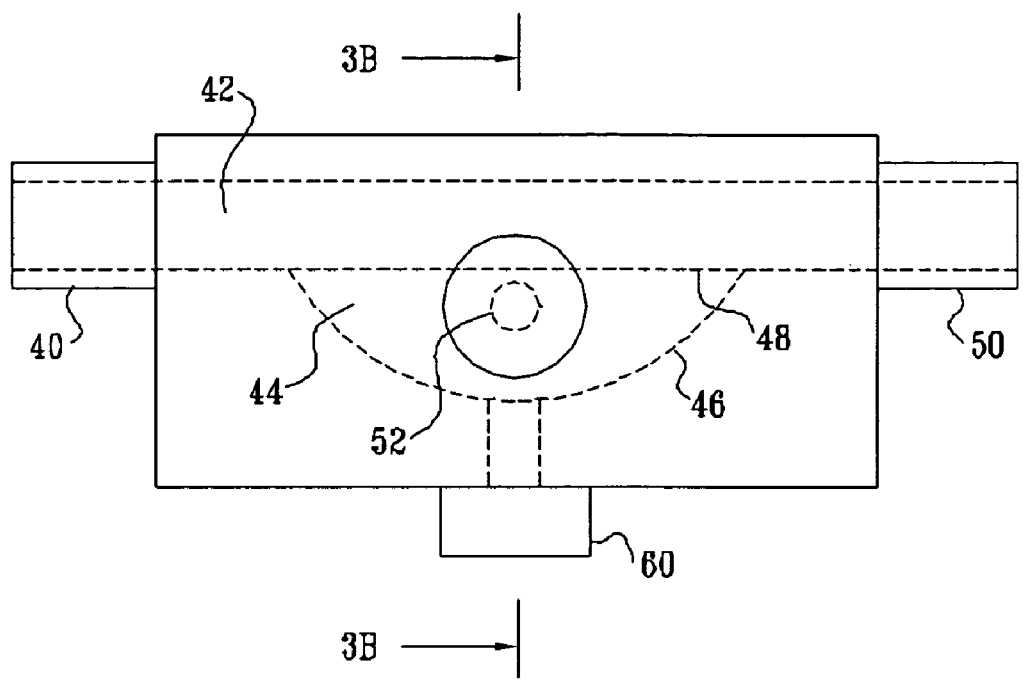
FIGS. 3A and 3B are schematic drawings of a sampling chamber according to another preferred embodiment of the present invention, for performing optical measurements on a sample of a flowing fluid.
Figure 3B:
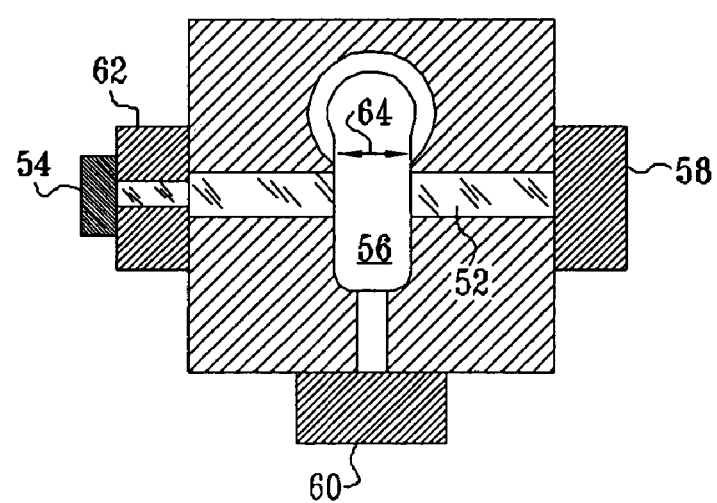

Referring now to FIGS. 3A and 3B, which are detailed schematic drawings of the sampling chamber 16 for performing optical measurements on a sample of a flowing fluid, as shown in FIG. 1, constructed and operative according to another preferred embodiment of the present invention. FIG. 3A is a side view of the sampling chamber. For the preferred embodiment of a milk sampler, the milk enters the sampling chamber, preferably directly from the milking machine, by means of an input tube or conduit, 40. Milk then flows along the main flow conduit 42. Adjoining the main flow conduit 42 is a recessed sample cavity 44, having a smooth profile 46 preferably in the shape of an arc of a circle. Cavity 44 is in fluid flow contact with main flow conduit 42 along a side wall 48 of the flow conduit 42. Milk flows out of sampling chamber 16 by means of an exit conduit or tube 50. During use, sampling chamber 16 is orientated such that sampling cavity 44 is located in a generally downwards direction. As a result, cavity 44 fills with a sample of the flowing milk. In particular, each new pulse of milk entering cavity 44 sweeps out the previous sample, replacing it with a new sample such that the sample is continually changed and each pulse is analyzed, regardless of the regularity with which the pulses arrive. The sampling process is thus virtually continuous. This property of the sampling chamber is particularly important for a milk farmer since the milk components can change during the course of a single milking of a cow, and only such a continuous sampler can easily track these changes in real time. This enables the milk farmer, for instance, to divert milk flow away from a main collection vat if any degradation in the milk quality is detected from its required standard.

Disposed generally near the center of sampling cavity 44, and below bottom wall 48 of the flow conduit 42, there is situated an orifice 52 in the body of the milk sampler 16, through which an optical beam enters sampling cavity 44. According to the preferred embodiment, orifice 52 is filled with an optically transparent solid through which the optical beam passes, thereby preventing flow of milk from orifice 52. Alternatively and preferably, light guides (not shown) disposed where orifice 52 meets sampling cavity 44 may be used for this purpose. On one side of orifice 52 there is a light source mount 54, in which or to which is attached LED illumination rosette 23 providing an incident optical beam. The optical beam measurement path traverses the central area 56 of recessed cavity 44, and orifice 52. Remote from the source 21 there is located a detector mounting 58 in which is installed in the transmission measurement detector 27, as seen in FIG. 1. According to a further preferred embodiment of the present invention, in addition to the transmission measurements, back-scattering measurements may be achieved by use of a detector located as close to the source as possible. This is achievable with mounting detector 24 at the center of the rosette 23, as seen in FIGS. 1 and 2, attached to sample chamber 16 by a mounting assembly 62. According to yet another preferred embodiment of the present invention, the optical measurement may be made by scattering other than back-scattering, and for this purpose another detector mount 60 is disposed, preferably at right angles to the optical beam path, to detect light scattered at 90 degrees by milk in sampling cavity 44. According to yet another preferred embodiment of the present invention, transmission detector 58 is replaced by another rosette 23 including both multiple light sources and a detector, as described above.

By means of milk sampler 16, shown in FIGS. 3A and 3B, it is possible to perform optical transmission measurements on a pulsating milk flow without the pulsation or turbulence significantly affecting the accuracy of measurement. Furthermore, the measurements can be made on-line and in real time, thus providing the farmer or milking data collection system with instant information about any change in the milk composition.

According to a further preferred embodiment of the present invention, sampling chamber 16 can be made to be the only part of the system installed in the potentially problematic environment of the milking stall (dirt, manure, water), the LED sources and the detectors, and the electronic units being installed remotely and connected by means of optical fibers or light guides and cables to sampling chamber 16. Furthermore, since the optical and electronic system does not need to perform analyses constantly during each milking, and also not, for instance, when the occupant of each stall is being changed, it is possible to multiplex several sample chambers in different milking stalls to one central optical and control system. As a result, even though the analyzer 16 is of low constructional cost compared with prior art analyzers, it becomes possible to even further reduce the cost to the farmer with a system which provides on-line milk analysis on the complete herd at the time of milking.

The width 64 of sampling cavity 44, is defined as the optical path length through which the optical beam passes within cavity 44. This optical path is an important parameter in determining the accuracy and sensitivity of the optical measurements on the sample. This is particularly relevant for a fluid such as milk which, because of its comparative opacity arising from the emulsive nature of milk, attenuates any incident optical beam in very short distances. This attenuation effect is also very dependent on the wavelength range used. The accuracy of the absorption measurement is inversely proportional to the distance a beam has to travel through the sample. For milk, for example, it is very difficult to accurately measure protein content for optical path lengths of more than approximately 2 mm. using direct absorption spectroscopy in the NIR-visible region. Thus, for instance, in the Tsenkova et al. article, it was noted that in the 700 to 1100 nm spectral region, though the best accuracy for fat determination was obtained with optical path lengths of 10 mm, in order to determine the protein content such a long optical path length resulted in an accuracy which was inadequate for practical application. An optical path length of 1 mm was found to be optimum for protein determination at those wavelengths. Though Tsenkova et al. found that the results in the 1100 to 2400 nm range were generally better than in the 700 to 1100 nm region, the latter region is to be preferred for use in a low cost instrument because of the wide availability of low cost sources and detectors. The analysis of milk at wavelengths below about 900 nm is particularly problematic because the flat and featureless nature of the milk spectrum in this region makes it difficult to obtain information from absorption measurements, such as are used in prior art methods.

Such conflicting measurement condition requirements may make it difficult to determine the optimum overall conditions for operation of a prior art spectrometric milk analyzer measuring only at the incident wavelength. In order to overcome the problem of the high optical absorption of milk, some prior art spectroscopic milk analysis methods use back scattering measurements only. This approach is problematic as well in that the real distance of penetration of the illumination is not really known, and the analysis results may therefore be inaccurate.

These problems are substantially reduced by the use of the preferred methods according to the present invention, where measurements of both transmission absorption, and of back reflection, substantially reduce the dependence on the sampling cavity width. Thus, in association with known electronic noise filtering techniques, it has been found that optical path lengths of 5 or 10 mm may be used, and these optical path lengths provide good accuracy for all of the components of milk. These methods have been found to be especially advantageous for protein measurements which, in order to provide accurate results, have generally been performed using narrow chambers of up to 2 mm with the prior art absorption methods.

Referring now to FIG. 4, which is a graph showing the results of approximately 140 analyses of samples of milk taken from different cows during milking for the protein content, using a milk analyzer constructed and operative according to preferred embodiments of the present invention. In FIG. 4, the protein concentration of the milk samples, accurately measured on a standard laboratory analytical instrument, are shown as small open circles. The protein concentrations measured on the milk analyzer, according to the embodiments of the present invention, are shown by the x symbols. As is observed, the results of the analyses obtained in real time using the analyzer of the present invention, are very close to those obtained on the laboratory analytical instrument. The standard deviation of the measurements is approximately 0.04%.

Referring now to FIG. 5, which is a graph showing the results of approximately 140 analyses of samples of milk for the somatic cell count (SCC) shown in units of thousands of cells detected, using a 10-LED milk analyzer constructed and operative according to preferred methods of the present invention. The SCC measurement is comparatively more difficult to perform accurately than the protein content analysis shown in FIG. 4, and yet the results shown in FIG. 5 indicate that the apparatus, according to embodiments of the present invention, is capable of providing even this measurement with good accuracy. The standard deviation of the SCC measurements is approximately 23.6.

Similar sets of measurements on approximately 150 samples of milk to analyze lactose, fat and urea content show similar levels of accuracy, with the values of the standard square deviation, $R^2$, being $R^2=0.970$, $R^2=0.992$ and $R^2=0.991$ respectively for these three sets of measurements.

It is thus observed from the above-mentioned results that the apparatus according to embodiments of the present invention, using inexpensive light sources and detectors, is capable of providing analysis of a flowing sample of milk, at the time of milking, with an accuracy which does not fall far from that of laboratory milk-analysis instruments.

It will be appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A sampling chamber for performing optical measurements on a sample of a flowing fluid, said chamber comprising:
   a flow conduit for the passage of fluid entering and exiting said sampling chamber;
   a recessed cavity having an arc-shaped smooth profile in fluid contact along a side wall of said conduit, and disposed in a generally downward direction such that a sample of the fluid in said conduit enters and exits said cavity so as to repeatedly replace the sample contained therein; and
   an optical transmission source for projecting an optical beam into said cavity, along an optical transmission path disposed outside the confines of said conduit.

2. A sampling chamber according to claim 1 wherein said optical transmission path includes at least one of optic fibers and plastic optical guides.

3. A sampling chamber according to claim 1 and wherein said recessed cavity is formed and disposed such that the fluid sample is repeatedly changed by the effects of the flow of the fluid in said conduit.

4. A sampling chamber according to claim 1 and wherein said recessed cavity is formed such that the optical measurements are generally unaffected by flow turbulence in said conduit.

5. A sampling chamber according to claim 1 and wherein said recessed cavity is formed such that the optical measurements are generally unaffected by flow pulsation in said conduit.

6. A sampling chamber according to claim 1, and wherein said conduit is a milk conduit.

7. A sampling chamber according to claim 1, and wherein the optical measurements are utilized to determine a relative concentration of at least one component of the fluid.

8. A sampling chamber according to claim 1 and wherein said optical transmission path comprises an entry port for projecting the optical beam from the optical source into said cavity through the fluid sample contained therein, and at least one exit port for directing the optical beam from said cavity to at least one exit detector.

9. A sampling chamber according to claim 8 and wherein said entry port and said exit port are disposed such that the optical beam traverses said cavity linearly, such that said exit detector measures optical transmission through the fluid sample contained in said cavity.

10. A sampling chamber according to claim 8 and wherein said exit port is disposed at a predetermined angle to the direction of the entering optical beam, such that said exit detector measures optical scattering through the fluid sample contained in said cavity.

11. A sampling chamber according to claim 8 and wherein said exit port is disposed essentially co-positional with said entry port such that said sampling chamber measures optical back-scattering from the fluid contained in said cavity.

12. A system for determining a concentration of at least one component of a fluid, the fluid comprising at least two components having different optical properties, said system comprising:
  a sampling chamber for performing optical measurements on a sample of a flowing fluid said chamber comprising:
    a flow conduit for the passage of fluid entering and exiting said sampling chamber;
    a recessed cavity having an arc-shaped smooth profile in contact along a side wall of said conduit, and disposed in a generally downward direction such that a sample of the fluid in said conduit enters and exits said cavity so as to repeatedly replace the sample contained therein; and
    an optical transmission path projecting an optical beam into said cavity, said optical transmission path disposed outside the confines of said conduit;
  a plurality of optical beam sources, at least one of which, when excited, emits an optical beam in an essentially continuum of wavelengths, at least two of said sources having different spectral ranges of emission, said sources being disposed such that the optical beam from said sources is incident to the fluid sample contained in said cavity;
  at least one detector selected from the group including
    a first detector disposed such that it measures the intensity of said optical beam transmitted through the fluid sample; and
    at least one second detector disposed such that it measures the intensity of said optical beam scattered by the fluid sample;
  a control system which serially causes excitation of at least two of said optical beam sources, such that the fluid is separately scanned with wavelengths of said optical beams emanating from said at least two optical beam sources; and
  a computing system operative to determine the concentration of the at least one component of the fluid from the intensity of at least one of the optical beams transmitted through the fluid and the optical beam scattered by the fluid sample.

13. A system according to claim 12, and wherein said plurality of optical beam sources is at least five sources.

14. A system according to claim 12, and wherein said plurality of optical beam sources is at least ten sources.

15. A system according to claim 12, and wherein said at least one second detector is disposed such that it measures the intensity of the optical beam reflected from the fluid sample.

16. A system according to claim 12, and wherein said sources are light emitting diodes.

17. A system according to claim 16 wherein the spectral half width of emission of at least one of said light emitting diodes is less than 40 nanometers.

18. A system according to claim 16, and wherein the spectral half width of emission of at least one of said light emitting diodes is less than 60 nanometers.

19. A system according to claim 12 and wherein said computing system is operative to determine the concentration of the at least one component by relating the intensity of said optical beam transmitted through the fluid sample and of said optical beam scattered by the fluid sample to an expression for the concentration in terms of the intensities.

20. A system according to claim 19 and wherein the expression is a polynomial expression of at least second order in the transmitted and scattered intensities.

21. A system according to claim 19 and wherein the transmitted and scattered intensities are related to the concentration of said at least one component by means of empirical coefficients, and wherein said empirical coefficients are determined by a statistical analysis of transmitted and scattered intensities obtained from a plurality of samples of the fluid having known concentrations of said at least one component.

22. A system according to claim 20, wherein the statistical analysis is a Partial Least Squares regression method.

23. The system of claim 21, wherein the statistical analysis is a Ridge Least Squares regression method.

24. The system of claim 21 wherein said empirical coefficients are stored in a database and the concentration is extracted from the transmitted and scattered intensities by means of statistical analysis methods operating on said database.

25. The system of claim 12 wherein said conduit is a milk conduit.

26. The system of claim 25, wherein said system determines the constitution of milk on-line during a milking process.

* * * * *